(12) United States Patent
Nicolas et al.

(10) Patent No.: US 10,717,987 B2
(45) Date of Patent: Jul. 21, 2020

(54) CUCURBITA PLANT RESISTANT TO POTYVIRUS

(71) Applicant: Syngenta Participations AG, Basel (CH)

(72) Inventors: Matthieu Nicolas, Sarrians (FR); Jean-Louis Nicolet, Sarrians (FR); Marc Oliver, Saint-Sauveur (FR); Sarah Danan, Saint-Sauveur (FR)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/437,632

(22) Filed: Jun. 11, 2019

(65) Prior Publication Data

US 2019/0309320 A1   Oct. 10, 2019

Related U.S. Application Data

(62) Division of application No. 14/112,657, filed as application No. PCT/EP2012/057075 on Apr. 18, 2012, now Pat. No. 10,351,874.

(30) Foreign Application Priority Data

Apr. 20, 2011   (EP) .................................... 11163208

(51) Int. Cl.
| | | |
|---|---|---|
| *C12N 15/82* | (2006.01) | |
| *A01H 5/10* | (2018.01) | |
| *C12Q 1/6895* | (2018.01) | |
| *A01H 5/08* | (2018.01) | |

(52) U.S. Cl.
CPC ........... *C12N 15/8283* (2013.01); *A01H 5/08* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| JP | 2002/536956 A | 11/2002 |
|---|---|---|
| JP | 2007/527717 A | 10/2007 |
| JP | 6209510 | 9/2017 |
| WO | 99/51749 | 10/1999 |
| WO | 2005/079162 | 9/2005 |
| WO | 2007/30356 | 3/2007 |
| WO | 2007030356 A2 | 3/2007 |

OTHER PUBLICATIONS

Brown, Rebecca N., et al., "Inheritance of resistance to four cucurbit viruses in Cucurbita moschata", Euphytica, Kluwer Academic Publishers, NL, vol. 129, No. 3, Jan. 1, 2003, pp. 253-258.
Paris, Harry S. and Brown, Rebecca N., "The Genes of Pumpkin and Squash", HortScience, 40(6): pp. 1620-1630, Oct. 2005.
Gilbert-Albertini, F. et al., "Resistance of Cucurbita moschata to watermelon mosaic virus type 2 and its genetic relation to resistance to zucchini yellow mosaic virus", Euphytica, 69, pp. 231-237, 1993.
Blanca, J. et al., Transcriptome characterization and high throughput SSRs and SNPs discovery in Cucurbita pepo (Cucurbitaceae), BMC Genomics, 12:104, pp. 1-15, 2011.
Sitterly, W. R., "Breeding for disease resistance in cucurbits," Annual Review of Phytopathology, Annual Reviews Inc., US, vol. 10, pp. 471-490, Jan. 1, 1972.
International Search Report and Written Opinion for International Patent Application No. PCT/EP2012/057075 dated Jul. 6, 2012.
Paris et al., "Oligogenic inheritance for resistance to Zucchini yellow mosaic virus in Cucurbita pepo," Ann. appl. Biol. (2000) 136:209-214.

*Primary Examiner* — Bratislav Stankovic
(74) *Attorney, Agent, or Firm* — Karen A. Magri

(57) ABSTRACT

The present invention relates to a *Cucurbita* plant, in particular a squash plant, having wide spectrum resistance to potyvirus such as Zucchini Yellow Mosaic Virus (ZYMV), Watermelon Mosaic Virus (WMV), *Papaya* Ringspot Virus (PRSV) and Moroccan watermelon mosaic virus (MWMV). Methods of selecting a squash plant having wide spectrum potyvirus resistance by marker assisted breeding are also provided.

9 Claims, 6 Drawing Sheets

Specification includes a Sequence Listing.

Pictures for Rating 1:

Pictures for Rating 2:

Pictures for Rating 3:

Picture for Rating 4

Pictures for Rating 5

Pictures for Rating 6

Pictures for Rating 7

Pictures for Rating 8

Pictures for Rating 9

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial
<220> FEATURE:
<223> OTHER INFORMATION: ZYMV-Nigeria forward primer

<400> SEQUENCE: 1
aggtttcatg ggcttttaat gg                                                   22

<210> SEQ ID NO 2
<211> LENGTH: 22
<212> TYPE: DNA
<213> ORGANISM: Artificial
<220> FEATURE:
<223> OTHER INFORMATION: ZYMV-Nigeria reverse primer

<400> SEQUENCE: 2
cgtgagccta aaacggttaa tg                                                   22

<210> SEQ ID NO 3
<211> LENGTH: 26
<212> TYPE: DNA
<213> ORGANISM: Artificial
<220> FEATURE:
<223> OTHER INFORMATION: QTL1 forward primer

<400> SEQUENCE: 3
gggcaaagaa gatcttgtct agaaag                                               26

<210> SEQ ID NO 4
<211> LENGTH: 23
<212> TYPE: DNA
<213> ORGANISM: Artificial
```

```
<220> FEATURE:
<223> OTHER INFORMATION: QTL1 reverse primer

<400> SEQUENCE: 4
gtttttgtgc agtgtgcatc tgt                                          23

<210> SEQ ID NO 5
<211> LENGTH: 25
<212> TYPE: DNA
<213> ORGANISM: Artificial
<220> FEATURE:
<223> OTHER INFORMATION: QTL2 forward primer

<400> SEQUENCE: 5
ttgtgtttat atgtatgtgt gcgag                                        25

<210> SEQ ID NO 6
<211> LENGTH: 28
<212> TYPE: DNA
<213> ORGANISM: Artificial
<220> FEATURE:
<223> OTHER INFORMATION: QTL2 reverse primer

<400> SEQUENCE: 6
tttctagatc tcagtgtaag agaacaca                                     28

<210> SEQ ID NO 7
<211> LENGTH: 17
<212> TYPE: DNA
<213> ORGANISM: Artificial
<220> FEATURE:
<223> OTHER INFORMATION: ZYMV Nigeria resistant allele specific probe

<400> SEQUENCE: 7
cacttcccag cccaaat                                                 17

<210> SEQ ID NO 8
<211> LENGTH: 17
<212> TYPE: DNA
<213> ORGANISM: Artificial
<220> FEATURE:
<223> OTHER INFORMATION: ZYMV-Nigeria susceptible allele specific probe

<400> SEQUENCE: 8
cactttccag cccaaat                                                 17

<210> SEQ ID NO 9
<211> LENGTH: 17
<212> TYPE: DNA
<213> ORGANISM: Artificial
<220> FEATURE:
<223> OTHER INFORMATION: QTL1 resistant allele specific probe

<400> SEQUENCE: 9
tcattgcacc caacatg                                                 17

<210> SEQ ID NO 10
<211> LENGTH: 18
<212> TYPE: DNA
<213> ORGANISM: Artificial
<220> FEATURE:
<223> OTHER INFORMATION: QTL1 susceptible allele specific probe

<400> SEQUENCE: 10
tcattgcact caacatgg                                                18
```

```
<210> SEQ ID NO 11
<211> LENGTH: 18
<212> TYPE: DNA
<213> ORGANISM: Artificial
<220> FEATURE:
<223> OTHER INFORMATION: QTL2 resistant allele specific probe

<400> SEQUENCE: 11
tttgtttgct tgagctgg                                                 18

<210> SEQ ID NO 12
<211> LENGTH: 18
<212> TYPE: DNA
<213> ORGANISM: Artificial
<220> FEATURE:
<223> OTHER INFORMATION: QTL2 susceptible allele specific probe

<400> SEQUENCE: 12
tttgttcgat tgagctgg                                                 18

<210> SEQ ID NO 13
<211> LENGTH: 21
<212> TYPE: DNA
<213> ORGANISM: Artificial
<220> FEATURE:
<223> OTHER INFORMATION: Ni+ forward primer

<400> SEQUENCE: 13
ttgcatgttc cttggatgggt                                              21

<210> SEQ ID NO 14
<211> LENGTH: 24
<212> TYPE: DNA
<213> ORGANISM: Artificial
<220> FEATURE:
<223> OTHER INFORMATION: Ni+ reverse primer

<400> SEQUENCE: 14
ggcaacctct gtccaatttctttc                                           24

<210> SEQ ID NO 15
<211> LENGTH: 15
<212> TYPE: DNA
<213> ORGANISM: Artificial
<220> FEATURE:
<223> OTHER INFORMATION: Ni+ resistant allele specific probe

<400> SEQUENCE: 15
agttgcgact ttcca                                                    15

<210> SEQ ID NO 16
<211> LENGTH: 17
<212> TYPE: DNA
<213> ORGANISM: Artificial
<220> FEATURE:
<223> OTHER INFORMATION: Ni+ susceptible allele specific probe

<400> SEQUENCE: 16
agttgcgact tttcatt                                                  17
```

US 10,717,987 B2

CUCURBITA PLANT RESISTANT TO POTYVIRUS

RELATED APPLICATIONS

This application is a divisional of co-pending U.S. application Ser. No. 14/112,657 (allowed), which claims priority under 35 U.S.C. § 371 from International Application No. PCT/EP2012/057075, filed Apr. 18, 2012, which claims the benefit of European Application No. EP 11163208.9, filed Apr. 20, 2011, the disclosures of which are incorporated by reference herein in their entirety.

SEQUENCE LISTING

A Sequence Listing in ASCII text format, submitted under 37 C.F.R. § 1.821, entitled "73202-US-REG-ORG-P-1_Seq_ListingFF_ST25.txt", 3.27 kb in size, generated on Apr. 17, 2012 and filed via EFS-Web is provided in lieu of a paper copy. This Sequence Listing is hereby incorporated by reference into the specification for its disclosures.

FIELD OF INVENTION

The present invention relates to novel plants resistant to potyvirus, and to seeds of said plants. The present invention also relates to methods of making such plants and for producing seeds thereof. The invention further relates to markers and the use thereof in marker assisted breeding.

The potyvirus group (named for its prototypical member, potato virus Y (PVY)) is the largest of the 34 plant virus groups and families currently recognised (Ward & Shukla, 1991; Intervirology 32, 269-296). This group contains at least 180 definitive and possible members (30% of all known plant viruses) which cause significant losses in agricultural, pastural, horticultural and ornamental crops (Ward & Shukla, 1991; Intervirology 32, 269-296).

A major problem in squash cultivation is the occurrence of potyvirus damaging plants and fruits. There are at least four potyvirus which most frequently infect squash—Zucchini Yellow Mosaic Virus (ZYMV), Watermelon Mosaic Virus (WMV), *Papaya* Ringspot Virus (PRSV), Moroccan watermelon mosaic virus (MWMV). The symptoms of potyvirus disease in squash include mosaicing, yellowing, shoestring leaves, stunting, and fruit and seed deformation.

Stable resistance to potyvirus is a key driver for squash breeders as viruses tend to mutate and overcome existing resistant genes. The only stable resistance known so far in squash, has been achieved throuh genetic modification approaches. In Europe, squash growers are increasingly seeing potyvirus infection in such "resistant" varieties. Thus, there is an unmet need for convenient and economically sustainable strategies to protect squash plants against potyvirus infection.

The present invention addresses this need by providing a squash plant with stable and wide resistance to different potyvirus generally affecting squash. This resistance is conferred by at least 3 recessive genetic determinants that have been introduced into a squash plant by classical interspecific crossing and embryo rescue.

SUMMARY OF INVENTION

The invention relates to a cultivated *Cucurbita* plant comprising at least one genetic determinant which is capable of directing or controlling resistance to potyvirus, preferably 1 or more of MWMV, PRSV, WMV and ZYMV.

In one embodiment, said genetic determinant is obtainable from the genome of *Cucurbita moschata*, preferably *C. moschata* var. Nigeria.

In another embodiment, the plant according to any of the previous embodiments comprises said at least one genetic determinant which is capable of directing or controlling resistance to potyvirus infection.

In another embodiment, the plant according to any of the previous embodiments comprises at least two genetic determinants which are capable of directing or controlling resistance to potyvirus infection.

In another embodiment, the plant according to any of the previous embodiments comprises at least three genetic determinants which are capable of directing or controlling resistance to potyvirus infection, preferably ZYMV and MWMV infection.

In another embodiment, the present invention relates to a plant according to any previous embodiment, wherein at least one of the genetic determinants is complementary to the corresponding genetic determinant present in *C. pepo* cv. 268NiW, representative seed of which is deposited at NCIMB under accession number NCIMB 41727, said corresponding genetic determinant being genetically linked to marker locus ZN, which co-segregates with the potyvirus resistance trait, preferably ZYMV and PRSV, and can be identified in a PCR by amplification of a DNA fragment with the pair of oligonucleotide primers: forward primer of SEQ ID NO: 1 (5' AGGTTTCATGGGCTTTTAATGG 3') and reverse primer of SEQ ID NO: 2 (5' CGTGAGC-CTAAAACGGTTAATG 3') followed by detection with resistant allele specific probe: FAM-CACTTCCCAGC-CCAAAT-MGB-NFQ (SEQ ID NO: 7) and/or susceptible allele specific probe: VIC-CACTTTCCAGCCCAAAT-MGB-NFQ (SEQ ID NO: 8); and/or at least two of the genetic determinants are complementary to the corresponding genetic determinants present in *C. pepo* cv. 268NiW, representative seed of which is deposited at NCIMB under accession number NCIMB 41727, said corresponding genetic determinants being genetically linked to marker locus W2, which co-segregates with the potyvirus resistance trait, preferably a MWMV resistance trait and can be identified in a PCR by amplification of a DNA fragment with the pair of oligonucleotide primers: forward primer of SEQ ID NO: 3 (5' GGGCAAAGAAGATCTTGTCTAGAAAG 3') and reverse primer of SEQ ID NO: 4 (5' GTTTTTGTGCA-GTGTGCATCTGT 3') followed by detection with resistant allele specific probe: FAM-TCATTGCACCCAACATG-MGB-NFQ (SEQ ID NO: 9) and/or susceptible allele specific probe: VIC-TCATTGCACTCAACATGG-MGB-NFQ (SEQ ID NO: 10); and/or forward primer of SEQ ID NO: 5 (5' TTGTGTTTATATGTATGTGTGCGAG 3') and reverse primer of SEQ ID NO: 6 (5' TTTCTAGATCTCAGTG-TAAGAGAACACA 3') followed by detection with resistant allele specific probe: FAM-TTTGTTTGCTTGAGCTGG-MGB-NFQ (SEQ ID NO: 11) and/or susceptible allele specific probe: VIC-TTTGTTCGATTGAGCTGG-MGB-NFQ (SEQ ID NO: 12) and/or.

at least one of the genetic determinants is complementary to the corresponding genetic determinant present in *C. pepo* cv. 268NiW, representative seed of which is deposited at NCIMB under accession number NCIMB 41727, said corresponding genetic determinant being genetically linked to marker locus Ni+, which co-segregates with the potyvirus resistance trait, preferably a ZYMV resistance trait, more preferably a ZYMV strain Nivir resistance trait, and can be identified in a PCR by amplification of a DNA fragment with the pair of oligonucleotide primers: forward primer of SEQ ID NO: 13 (5' TTGCATGTTCCTTGGATGGGT 3') and reverse primer of SEQ ID NO: 14 (5' GGCAACCTCTGTC-CAATTTCTTTC 3') followed by detection with resistant allele specific probe: FAM-AGTTGCGACTTTCCA-MGB-NFQ (SEQ ID NO: 15) and/or susceptible allele specific probe: TET-AGTTGCGACTTTTCATT-MGB-NFQ (SEQ ID NO: 16)

In another embodiment, the present invention relates to a plant according to any previous embodiment, wherein the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus ZN which co-segregates with the potyvirus resistance trait, preferably a ZYMV and PRSV resistance trait, and can be identified in the *C. pepo* cv. 268NiW genome in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8;

and/or the genetic determinants are complementary to the corresponding genetic determinants present in *C. pepo* cv. 268NiW, representative seed of which is deposited at NCIMB under accession number NCIMB 41727, said corresponding genetic determinant being genetically linked to marker loci W1 and W2 which co-segregates with the potyvirus resistance trait, preferably a MWMV resistance trait and can be identified in the *C. pepo* cv. 268NiW genome in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10 and/or forward primer of SEQ ID NO: 5 and reverse primer of SEQ ID NO: 6 followed by detection with SEQ ID NO:11 and/or SEQ ID NO:12; and/or the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus Ni+ which co-segregates with the potyvirus resistance trait, preferably a ZYMV resistance trait, more preferably a ZYMV strain Nivir resistance trait, and can be identified in the *C. pepo* cv. 268NiW genome in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16.

In another embodiment, the present invention relates to a plant according to any previous embodiment, wherein the genetic determinant is genetically linked to marker locus ZN, which co-segregates with the potyvirus resistance trait, preferably a ZYMV and PRSV resistance trait, and can be identified in the genome of said plant in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8; and/or the genetic determinant is genetically linked to marker locus W1 and/or W2, which co-segregates with the potyvirus resistance trait, preferably a MWMV resistance trait and can be identified in the genome of said plant in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10; and/or forward primer of SEQ ID NO: 5 and reverse primer of SEQ ID NO: 6 followed by detection with SEQ ID NO:11 and/or SEQ ID NO:12; and/or the genetic determinant is genetically linked to marker locus Ni+, which co-segregates with the potyvirus resistance trait, preferably a ZYMV resistance trait, more preferably a ZYMV strain Nivir resistance trait, and can be identified in the genome of said plant in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16.

In another embodiment, the present invention relates to a plant according to any previous embodiment, wherein the genetic determinant(s) is/are recessive and segregate independently of one another.

In another embodiment, the present invention relates to a plant according to any previous embodiment, wherein the plant is a squash plant.

The invention also relates to seed of a squash plant according to any previous embodiment which is capable of growing a potyvirus resistant squash plant. The invention also relates to use of a said seed for growing a potyvirus resistant squash plant.

The invention also relates to a method for producing a squash plant exhibiting resistance to potyvirus, preferably at least one of MWMV, PRSV, WMV and ZYMV comprising the steps of:

a) Selecting a squash plant comprising at least one genetic determinant which is capable of directing or controlling resistance to potyvirus, wherein said genetic determinant is obtainable from the genome of *C. pepo* cv. 268NiW and is genetically linked to at least one marker locus, which co-segregates with resistance to potyvirus, and can be identified in a PCR by at least one pair of PCR oligonucleotide primers comprising i. forward primer of SEQ ID NO: 1 and reverse primer of SEQ ID NO: 2 followed by detection with SEQ ID NO:7 and/or SEQ ID NO:8, and/or;

ii. forward primer of SEQ ID NO: 3 and reverse primer of SEQ ID NO: 4 followed by detection with SEQ ID NO:9 and/or SEQ ID NO:10, and/or;

iii. forward primer of SEQ ID NO: 5 and reverse primer of SEQ ID NO: 6 followed by detection with SEQ ID NO:11 and/or SEQ ID NO:12, and/or;

iv. forward primer of SEQ ID NO: 13 and reverse primer of SEQ ID NO: 14 followed by detection with SEQ ID NO:15 and/or SEQ ID NO:16, and/or v. a forward and reverse primer capable of identifying a marker locus which co-segregates with resistance to potyvirus;

b) Crossing said plant of step a) with a squash plant which is susceptible to potyvirus, or exhibits an intermediate level of resistance to at least one of said potyviruses; and c) Selecting a progeny from said cross which exhibits a resistance phenotype to potyvirus, and wherein said resistance phenotype(s) segregates with said at least one marker locus of step a).

The invention also relates to a method for producing a squash plant exhibiting resistance to potyvirus, according to any previous embodiment, comprising the steps of:

a) Selecting a squash plant comprising at least one genetic determinant which is capable of directing or controlling resistance to potyvirus, preferably at least one of ZYMV and MWMV wherein said genetic determinant is obtainable from the genome of *C. pepo* cv. 268NiW and is genetically linked to at least one marker locus, which co-segregates with potyvirus resistance, and can be identified in a PCR by at least one pair of PCR oligonucleotide primers comprising
  i. Forward primer of SEQ ID NO: 1 and reverse primer of SEQ ID NO: 2 followed by detection with SEQ ID NO:7 and/or SEQ ID NO:8 if the marker locus is ZN, or;
  ii. Forward primer of SEQ ID NO: 3 and reverse primer of SEQ ID NO: 4 followed by detection with SEQ ID NO:9 and/or SEQ ID NO:10 and/or
  iii. Forward primer of SEQ ID NO: 5 and reverse primer of SEQ ID NO: 6 followed by detection with SEQ ID NO:11 and/or SEQ ID NO:12 if the marker locus is W2 and/or
  iv. Forward primer of SEQ ID NO: 13 and reverse primer of SEQ ID NO: 14 followed by detection with SEQ ID NO:15 and/or SEQ ID NO:16 if the marker locus is Ni+;
  b) Crossing said plant of step a) with a squash plant which is susceptible to potyvirus, or exhibits an intermediate level of resistance to at least one of said potyviruses; and
  c) Selecting a progeny from said cross which exhibits a resistance phenotype to potyvirus, and wherein said resistance phenotype(s) segregates with said at least one marker locus of step a).

In one embodiment, the present invention relates to a method according to any previous embodiment, wherein the plant selected in step a) comprises at least two genetic determinants which are capable of directing or controlling resistance to potyvirus; and the selected progeny in step c) exhibits a resistance phenotype to potyvirus, preferably ZYMV and MWMV and wherein said resistance phenotypes segregate with two marker loci of step a).

In another embodiment, the present invention relates to a method according to any previous embodiment, wherein the plant selected in step a) comprises at least three genetic determinants which are capable of directing or controlling resistance to potyvirus, preferably ZYMV and MWMV; and the selected progeny in step c) exhibits a resistance phenotype to potyvirus, preferably ZYMV and MWMV and wherein said resistance phenotypes segregate with three marker loci of step a).

In another embodiment, the present invention relates to a method according to any previous embodiment, wherein the donor plant of step a) is a plant as described herein.

In another embodiment, the present invention relates to a method according to any previous embodiment, comprising the additional step of backcrossing the virus resistant plant obtained in step c) with the susceptible squash plant, or intermediate resistant squash plant, of step b).

The invention also relates to a method for producing hybrid seeds of squash resistant to potyvirus comprising planting a male-sterile female plant and a male-fertile plant, wherein at least one of said male or female line is a plant as described herein, effecting cross pollination between both lines, growing the plant till fruit setting, collecting the fruits and obtaining the hybrid seeds.

The invention also relates to a method for obtaining a potyvirus resistant squash plant comprising
  a) obtaining a plant as described herein or by a method as described herein;
  b) Crossing said plant with a potyvirus susceptible plant or an intermediate resistant squash plant;
  c) Rescuing an embryo resulting from the cross of step b);
  d) Regenerating a plant from said embryo of step c); and
  e) Selecting a plant of step d) that is resistant to potyvirus.

The invention also relates to a method for obtaining squash fruit resistant to potyvirus comprising sowing seed of a plant as described herein or obtained by a method as described herein; and growing said plant in order to produce fruit and harvesting the fruit produced by said plant.

The invention also relates to a genetic determinant which is capable of directing or controlling resistance to potyvirus wherein said genetic determinant is obtainable from the genome of *C. pepo* cv. 268NiW, and wherein
  the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus ZN, which co-segregates with the potyvirus resistance trait, preferably a ZYMV and PRSV resistance trait, and can be identified in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8; and/or
  the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus W2, which co-segregates with the potyvirus resistant trait, preferably a MWMV resistance trait and can be identified in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10
  and/or forward primer of SEQ ID NO: 5 and reverse primer of SEQ ID NO: 6 followed by detection with SEQ ID NO:11 and/or SEQ ID NO:12; and/or
  the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus Ni+, which co-segregates with the potyvirus resistance trait, preferably a ZYMV resistance trait, more preferably a ZYMV strain Nivir resistance trait, and can be identified in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16.

The invention also relates to a method of identifying a squash plant comprising at least one genetic determinant which is capable of directing or controlling resistance to potyvirus, preferably to at least one of ZYMV and MWMV wherein said genetic determinant is obtainable from the genome of *C. pepo* cv. 268NiW and is genetically linked to at least one marker locus, which co-segregates with at least one of said potyvirus resistant phenotypes and can be identified in a PCR by at least one pair of PCR oligonucleotide primers comprising
  forward primer of SEQ ID NO: 1 and reverse primer of SEQ ID NO: 2 followed by detection with SEQ ID NO:7 and/or SEQ ID NO:8 if the marker locus is ZN, or;
  forward primer of SEQ ID NO: 3 and reverse primer of SEQ ID NO: 4 followed by detection with SEQ ID NO:9 and/or SEQ ID NO:10 if the marker locus is W1 and/or
  forward primer of SEQ ID NO: 5 and reverse primer of SEQ ID NO: 6 followed by detection with SEQ ID NO:11 and/or SEQ ID NO:12 if the marker locus is W2; or;

forward primer of SEQ ID NO: 13 and reverse primer of SEQ ID NO: 14 followed by detection with SEQ ID NO:15 and/or SEQ ID NO:16 if the marker locus is Ni+.

The invention also relates to the use of potyvirus resistant propagating material from a squash plant as described herein for growing a potyvirus resistant squash plant in order to produce fruit and harvest said fruit.

DEFINITIONS

Figure 1:
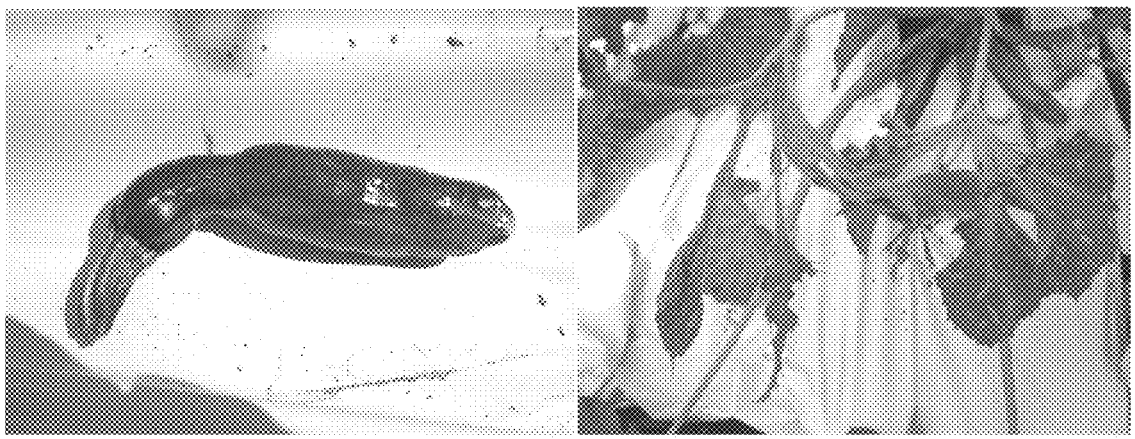
FIG. 1 provides photographs showing examples of plants having a potyvirus disease rating of 1 (see Table 1).
Figure 2:
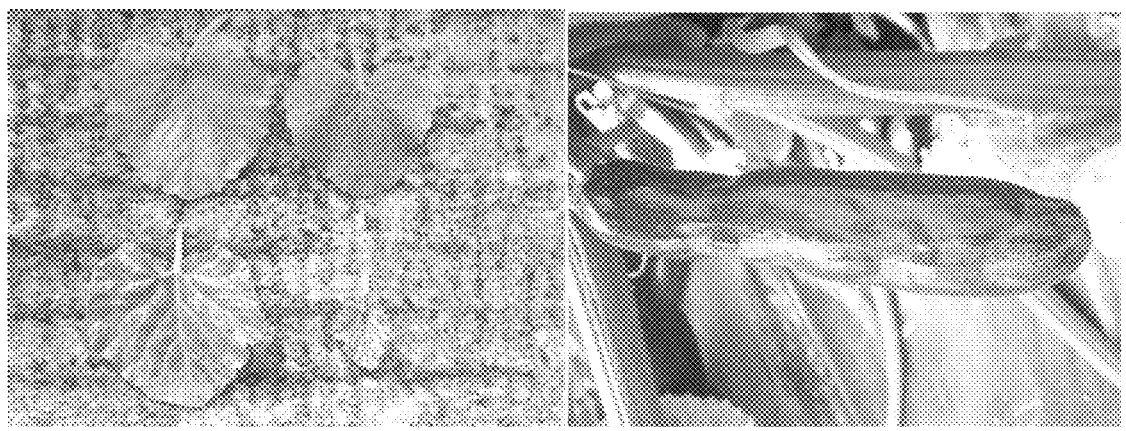
FIG. 2 provides photographs showing examples of plants having a potyvirus disease rating of 2 (see Table 1).
Figure 3:
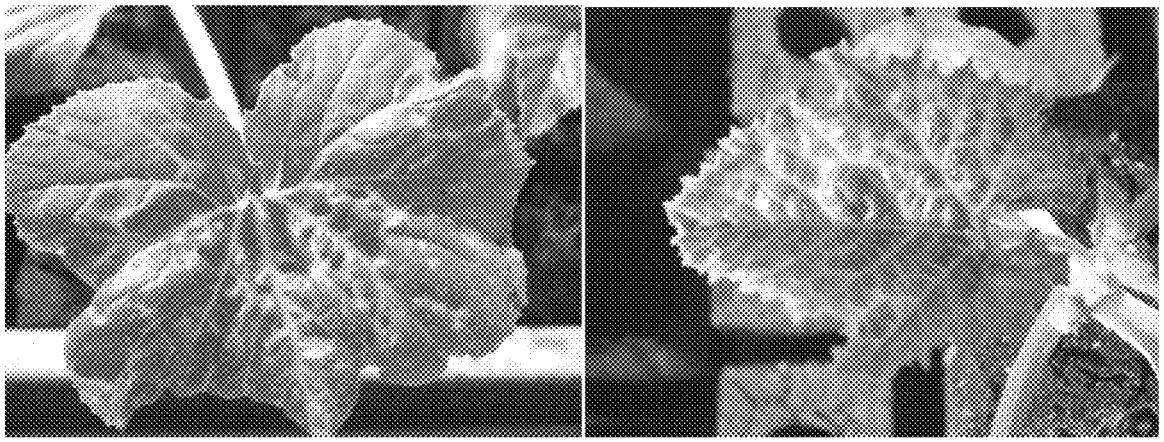
FIG. 3 provides photographs showing examples of plants having symptoms corresponding to a potyvirus disease rating of 3 (see Table 1).
Figure 4:
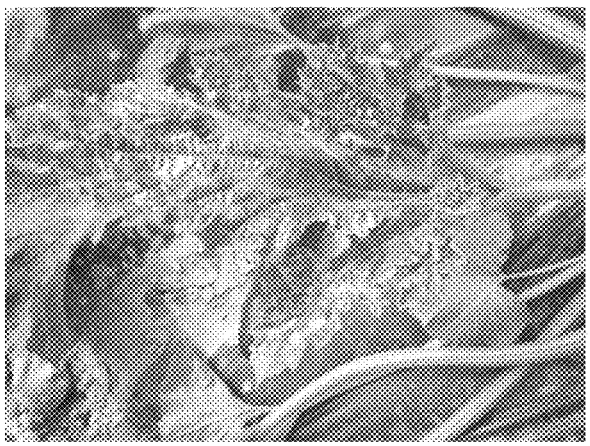
FIG. 4 provides that showing examples of plants having symptoms corresponding to a potyvirus disease rating of 4 (see Table 1).
Figure 5:
FIG. 5 provides photographs showing examples of plants having symptoms corresponding to a potyvirus disease rating of 5 (see Table 1).
Figure 5:
Figure 5:
Figure 6:
FIG. 6 provides photographs showing examples of plants having symptoms corresponding to a potyvirus disease rating of 6 (see Table 1).
Figure 7:
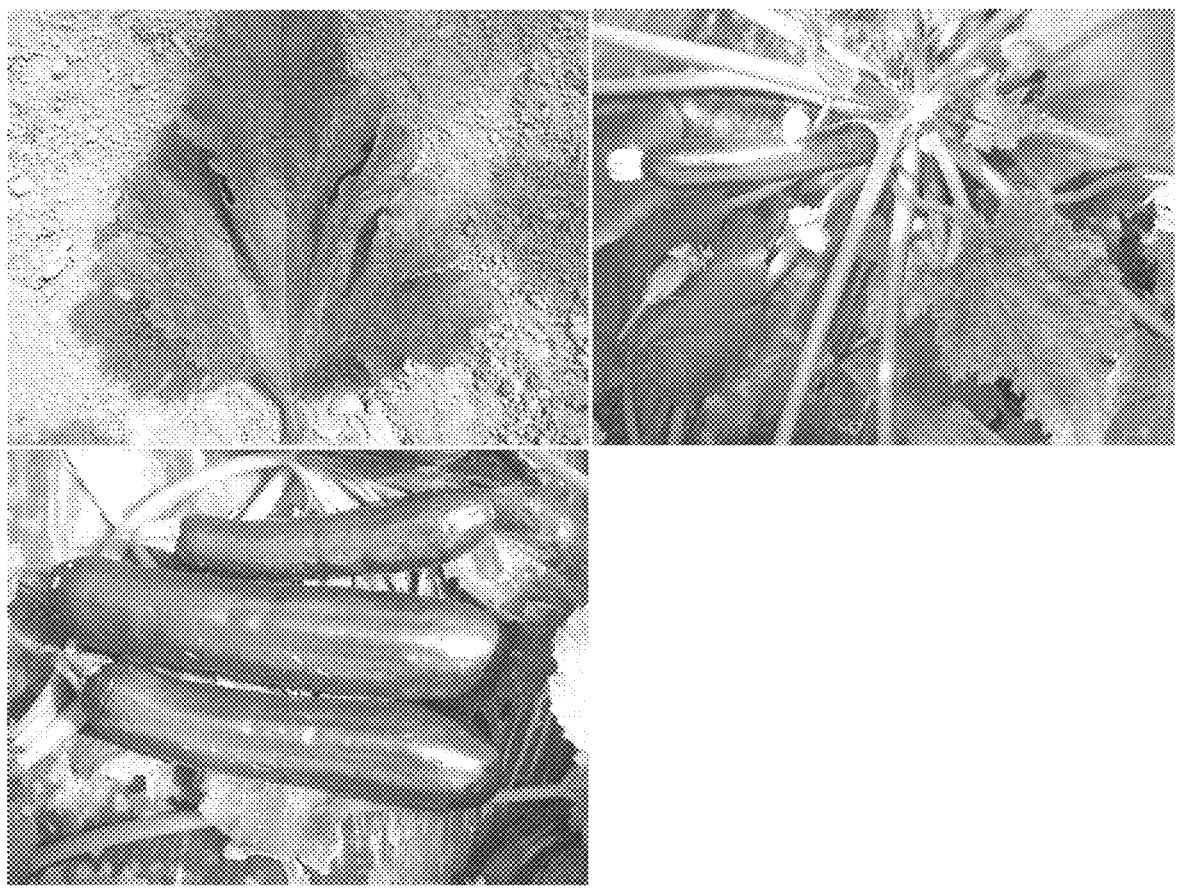
FIG. 7 provides photographs showing examples of plants having symptoms corresponding to a potyvirus disease rating of 7 (see Table 1).
Figure 8:
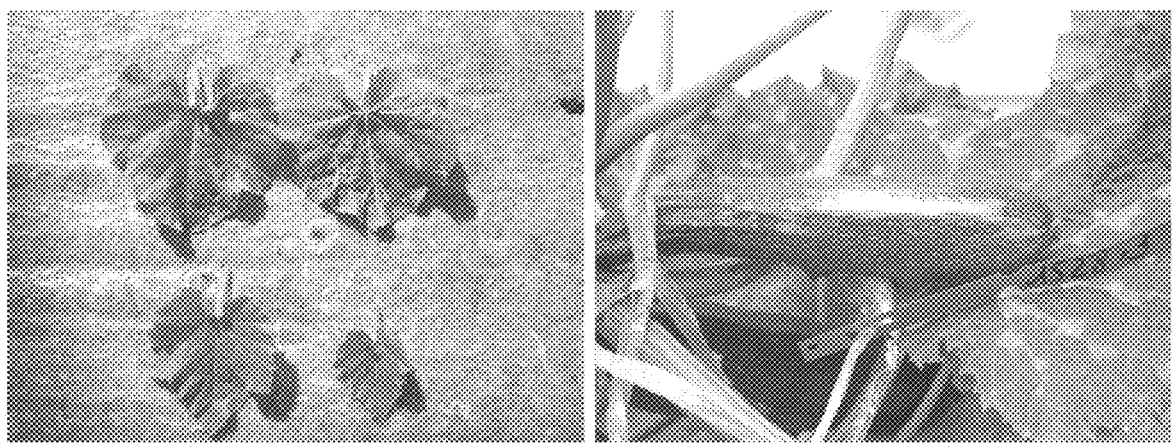
FIG. 8 provides photographs showing examples of plants having symptoms corresponding to a potyvirus disease rating of 8 (see Table 1).
Figure 9:
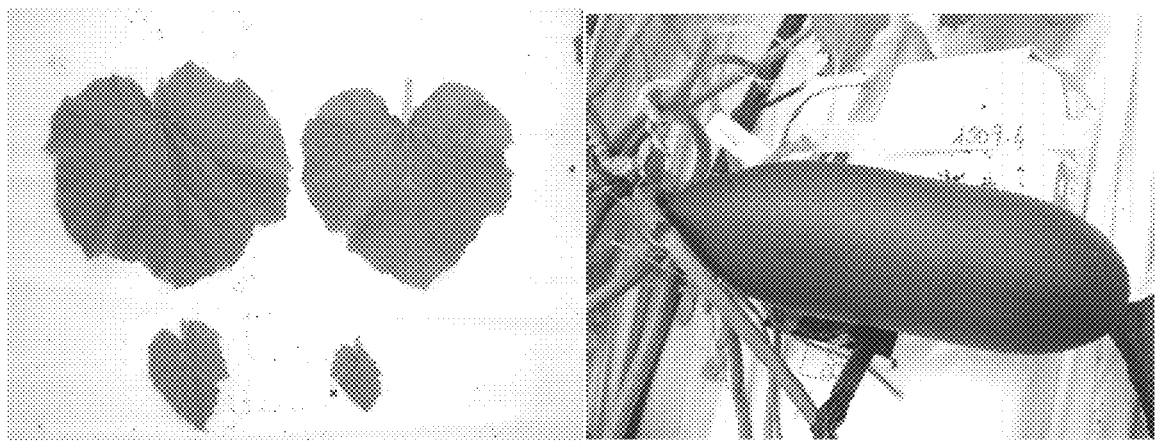
FIG. 9 provides photographs showing examples of plants having symptoms corresponding to a potyvirus disease rating of 9 (see Table 1).

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

A cultivated *Cucurbita pepo* plant is understood within the scope of the invention to refer to a plant that is no longer in the natural state but has been developed and domesticated by human care and for agricultural use and/or human consumption. As a matter of example, *C. pepo* plant according to the present invention is to be regarded as a cultivated plant and can be selected from the group comprising gem squash, summer squash, winter squash, zucchini, yellow crookneck squash, yellow summer squash, cocozelle, scallop, straightneck and vegetable marrow. In the context of the present invention, a "cultivated *Cucurbita pepo* plant" is adapted to cultivation and exhibits disease resistance, particularly Intermediate Resistance, such as Zucchini Yellow Mosaic Virus (ZYMV) Intermediate Resistance. Cultivated *Cucurbita* plants are further understood to exclude those wild-type species which comprise the trait being subject of this invention as a natural trait and/or part of their natural genetics.

For the avoidance of doubt, C. *Moschata* var. Nigeria is a "wild source" of resistance and is not to be regarded as a cultivated plant.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

The phrase "genetically linked to marker locus" is to be regarded as meaning the marker locus is no further than 10 cM, more preferably 5 cM, more preferably, 2 cM, most preferably 1 cM from the genetic determinant conferring the resistance trait.

A "genetic determinant directing or controlling expression" is understood herein to refer to a heritable genetic element that is capable of contributing to the expression of a trait on the level of the DNA itself, on the level of translation, transcription and/or activation of a final polypeptide product, leading to the phenotypic expression of the trait.

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "genetic architecture at the qualitative trait locus" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorph isms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

The phrase "complementary to the corresponding genomic determinant present in C. Pepo cv. 268NiW" is to be regarded as meaning a gene (or promoter region thereof) found on a region of chromosomal DNA, said region being 0.5 MB, 1 MB, 2 MB, 3 MB, 4 MB, 5 MB or 10 MB in length, which is identical to the same gene (or promoter region thereof) found on the corresponding region of C. Pepo cv. 268NiW chromosomal DNA.

A genetic marker can be physically located in a position on a chromosome that is within or outside of the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative or qualitative trait as defined herein). Thus, in some embodiments a genotype comprises a summary of one or more alleles present within an individual at one or more genetic loci of a quantitative or qualitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross F1 hybrid" refers to an F1 hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the term "dihaploid line", refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating anymore (stable).

As used herein, the term "linkage", and grammatical variants thereof, refers to the tendency of alleles at different loci on the same chromosome to segregate together more often than would be expected by chance if their transmission were independent.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an individual, resulting from the interaction of its genome, proteome and/or metabolome with the environment.

As used herein, the phrase "resistance" refers to the ability of a plant to restrict the growth and development of a specified pathogen and/or the damage they cause when compared to susceptible plants under similar environmental conditions and pathogen pressure. Resistant plants may exhibit some disease symptoms or damage under pathogen pressure, e.g. ZYMV pathogen pressure.

As used herein, the phrase "susceptibility" refers to the inability of a plant to adequately restrict the growth and development of a specified pathogen, e.g. potyvirus pathogen such as ZYMV.

Resistant plants will show no or very few necroses with no or very sparse sporulation under the test conditions defined in the Examples below.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the F1, the F2, or any subsequent generation.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, fruit color, and several known disease resistances.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labeled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 5371 1). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program 'fasta20u66" (version 2.0u66, September 1998 by William R. Pearson and the University of Virginia; see also W. R. Pearson (1990), Methods in Enzymology 183, 63-9a, appended examples). For this purpose, the "default" parameter settings may be used. Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The thermal melting point is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 650 for 15 minutes (see Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" or "plant material obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

DETAILED DESCRIPTION OF THE INVENTION

The present invention relates to novel squash plants, which are resistant to potyvirus infection and thus protected from damage caused by this pathogen. The present invention also relates to methods of making and using such plants.

Plants according to the invention may be obtained by crossing two or more parental genotypes, at least one of which may have one or more alleles, particularly one or more alleles at corresponding loci contributing to potyvirus resistance, which allele(s) is/are lacking in the other parental genotype or which complements the other genotype to obtain a plant according to the invention and as described herein. If more than one loci contribute to the expression of the resistance trait and the two original parental genotypes do not provide the entire set of alleles, other sources can be included in the breeding population. The other parental genotype may contribute a desirable trait including crop quality demanded by the market.

The parental genotypes may be crossed with one another to produce progeny seed. The parental genotypes may be inbred lines developed by selfing selected heterozygous plants from fields with uncontrolled or open pollination and employing recurrent selection procedures. Superior plants are selfed and selected in successive generations. In the succeeding generations the heterozygous condition gives way to homogeneous lines as a result of self-pollination and selection. With successive generations of inbreeding, the plant becomes more and more homozygous and uniform within the progeny plants. Typically, five to seven or more generations (F1 to F2; F3 to F4; F4 to F5) of selfing and pedigree selection may be practiced to obtain inbred lines that are uniform in plant and seed characteristics and that will remain uniform under continued self-fertilization.

During inbreeding, many undesirable alleles at heterozygous loci will be replaced by more favourable alleles and the unfavourable or undesired alleles eliminated from the progeny. Moreover, through marker-based selection the number of favorable alleles can be maximized in that the more unfavourable alleles are identified and successively replaced by the more favorable alleles.

In one aspect, the plant according to the invention may be obtained by introgressing a genetic determinant capable of directing or controlling resistance to potyvirus from an ancestor plant, particularly a wild ancestor plant into a cultivated squash plant, particularly a cultivated *Cucurbita pepo* plant.

In one specific embodiment of the invention, the wild ancestor, from which the genetic determinant(s) capable of directing or controlling resistance to potyvirus may be obtained, is wild *C. moschata*, particularly wild *C. moschata* var. Nigeria, or from a progeny or an ancestor thereof comprising said genetic determinant(s). The potyvirus resistance trait according to the present invention, which confers to a plant expressing this trait, resistance to potyvirus infection, preferably to 1 or more of MWMV, PRSV, WMV and ZYMV, may, in the alternative, be obtained from *C. pepo* cv. 268NiW, representative seed of which is deposited at NCIMB under Accession No. NCIMB 41727, or from a progeny or ancestor of *C. pepo* cv. 268NiW comprising a genetic determinant capable of directing or controlling resistance to potyvirus.

Figure 10:
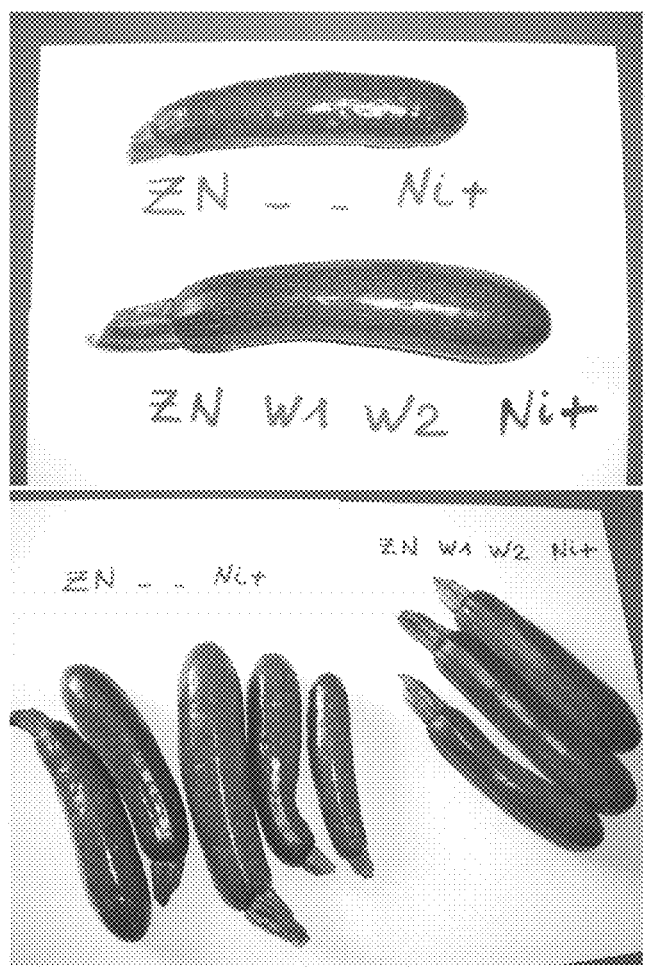
FIG. 10 provides photographs showing the level of potyvirus resistance for squash plants comprising determinants Zn and Ni+(top panel), or Zn, Ni+, W1 and W2 (bottom panel).

Accordingly, in a specific embodiment of the invention, the parental genotype contributing to the potyvirus resistance trait(s) is an inbred line having the invention relevant properties of deposited *C. pepo* cv. 268NiW, i.e. substantially the same genome architecture at the locus associated with potyvirus resistance, seed samples of which have been deposited on 14th June 2010 with NCIMB under accession number NCIMB 41727. *C. pepo* cv. 268NiW is resistant to MWMV, PRSV, WMV and ZYMV. Resistance is provided by the genetic determinants Zn, Ni+, W1 and W2. These determinants are homozygous recessive in 268NiW. These determinants are transferable between multiple genetic backgrounds. Resistance assays have demonstrated that these genetic determinants continue to provide wide spectrum resistance to potyviruses in these different backgrounds e.g. Caserta, yellows. The level of resistance to the different potyvirus strains is shown in Table 2. The beneficial effect of having all 4 genetic determinants when the plant is challenged with potyvirus is shown in Table 2 and FIG. 10.

To determine the utility of the inbred line and its potential to genetically contribute to the hybrid progeny a test-cross is made with another inbred line, and the resulting progeny phenotypically evaluated.

In another specific embodiment of the invention, the parental genotype contributing to the resistance trait(s) is a hybrid having the invention relevant properties of deposited *C. pepo* cv. 268NiW, i. e. substantially the same genome architecture at the locus associated with potyvirus resistance, seed samples of which have been deposited on 14 Jun. 2010 with NCIMB under accession number NCIMB 41727.

*C. pepo* cv. 268NiW resulted from a cross of a wild *C. moschata* var. Nigeria as the donor of the potyvirus resistance trait with a *C. pepo* inbred line. Potyvirus resistant progeny of this cross were crossed with further inbred lines of different genetic backgrounds to finally obtain *C. pepo* cv. 268NiW.

Accordingly, *C. pepo* cv. 268NiW or any other plant line containing a genetic determinant capable of directing or controlling resistance to potyvirus may be used as a source material for introgressing said resistance trait into any desired genetic background to obtain a squash plant being highly resistant to potyvirus infection according to the invention, may further contain one or more desirable traits such as crop quality traits demanded by the market. Beside crop quality, agronomically important characteristics such as, for example, a good plant architecture, high productivity and basic resistances to pathogens.

Based on the description of the present invention, the skilled person who is in possession of *C. pepo* cv. 268NiW, a sample of which has been deposited with NCIMB Ltd under accession number NCIMB 41727 or of a progeny or ancestor thereof containing at least one genetic determinant capable of directing or controlling resistance to potyvirus, as described herein, has no difficulty to transfer the said at least one genetic determinant of the present invention to other squash plants of various types using breeding techniques well-known in the art. The trait of the present invention may for example be transferred to other *Cucurbita* species Accordingly, in one embodiment, a plant of the present invention is a squash plant capable of resisting potyvirus infection. In one embodiment of the invention, the squash plants are grown for (hybrid) seed or commercial squash production.

Accordingly, in another embodiment, the present invention discloses a method of transferring the at least one genetic determinant capable of directing or controlling resistance to potyvirus according to the present invention to a squash plant lacking said trait comprising a) obtaining a plant comprising said trait; b) crossing it to a plant lacking said trait; c) obtaining plants of the cross of step b); d) selecting a plant of step c) which is capable of resisting potyvirus infection according to the present invention. In one embodiment, the method further comprises e) back-crossing a plant resulting from step d) with a squash plant, and f) selecting for a squash plant, which is capable of resisting potyvirus infection according to the present invention. In one embodiment, the method further comprises obtaining an inbred squash plant, which is capable of resisting potyvirus infection according to the present invention, and, in one embodiment, the method further comprises crossing said inbred squash plant to another squash plant to produce a hybrid squash plant, which is capable of resisting potyvirus infection according to the present invention. In one embodiment, a squash plant is selected by determining the presence or absence of the potyvirus, as described herein. In one embodiment, the plant of step a) comprising said trait is *C. pepo* cv. 268NiW, representative seed of which is deposited at NCIMB under Accession No. NCIMS 41727, or a progeny or ancestor of said plant.

Marker-assisted breeding may also be employed to identify those individuals which contain the at least one genetic determinant capable of directing or controlling resistance to potyvirus, and/or flanking marker loci or marker loci genetically linked thereto, as described herein.

Marker-based selection may already be used in the early phases of inbred development, often in combination with screening methods which are based largely on phenotypic characteristics that can be determined visually and are related to key performance indices which are relevant for the suitability of the plant to be utilized in commercial hybrid production. Selection may also be based on molecular markers, which may or may not be linked to traits of interest.

In particular, marker-based selection may be applied in combination with or followed by a phenotypic selection to identify those individuals where all of the invention relevant loci described herein before have homozygous favorable genotypes.

There are several types of molecular markers that may be used in marker-based selection including, but not limited to, restriction fragment length polymorphism (RFLP), random amplification of polymorphic DNA (RAPD), and amplified restriction fragment length polymorphism (AFLP).

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, techniques to visualize the obtained fragments, up to 100 polymorphic loci can be measured per primer combination and only small DNA samples are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for SSR analysis. SNPs use PCR extension assays that efficiently pick up point mutations. The procedure requires little DNA per sample. One or two of the above methods may be used in a typical marker-based selection breeding program.

The most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form.

Alternative methods may be employed to amplify fragments, such as the "Ligase Chain Reaction" ("LCR") (Barany, Proc. Natl. Acad. SCi. (U.SA) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90101069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endonuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavage, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The cleavage reaction is highly specific, has a low failure rate, and can detect zeptomol quantities of target DNA. While the assay traditionally has been used to interrogate one SNP in one sample per reaction, novel chip- or bead-based approaches have been tested to make this an efficient and accurate assay adaptable to multiplexing and high-throughput SNP genotyping.

Nickerson et al. have described a nucleic acid detection assay that combines attributes of PCR and OLA (Nickerson et al., Proc. Natl. Acad. Sci. (U.S.A.) 87:8923 8927 (1990)). In this method, PCR is used to achieve the exponential amplification of target DNA, which is then detected using OLA.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560 569 (1989)), and may be readily adapted to the purposes of the present invention.

In one embodiment, a molecular marker is a DNA fragment amplified by PCR, e.g. a SSR marker or a RAPD marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait.

In a specific embodiment of the invention SNP markers are used to identify genetic determinants of the present invention capable of directing or controlling resistance to potyvirus in the parent plants and/or the ancestors thereof, as well as in the progeny plants resulting from a cross of said parent plants. SNP markers are detectable by End Point reading Taqman technology and, in addition to specific forward and reverse primer sequences, probes (for example as herein disclosed) can be used to detect the presence of the R and/or S allele at each of the marker loci. So, each of the disclosed genetic markers are composed of four and not just two sequences: the forward and reverse primers which amplify the target region and the two probes which identify the target SNP.

In the present invention, one or more DNA markers of the present invention which co-segregates with resistance to potyvirus, can be identified in a PCR by at least one pair of PCR oligonucleotide primers comprising of
  i. Forward primer of SEQ ID NO: 1 and reverse primer of SEQ ID NO: 2 followed by detection with SEQ ID NO:7 and/or SEQ ID NO:8, and/or;
  ii. Forward primer of SEQ ID NO: 3 and reverse primer of SEQ ID NO: 4 followed by detection with SEQ ID NO:9 and/or SEQ ID NO:10, and/or;
  iii. Forward primer of SEQ ID NO: 5 and reverse primer of SEQ ID NO: 6 followed by detection with SEQ ID NO:11 and/or SEQ ID NO:12, and/or
  iv. Forward primer of SEQ ID NO: 13 and reverse primer of SEQ ID NO: 14 followed by detection with SEQ ID NO:15 and/or SEQ ID NO:16
said primers leading to an amplification product in a PCR reaction exhibiting a molecular weight or a nucleotide sequence, which is essentially identical or can be considered as an allele to that of a corresponding PCR amplification product obtainable from *C. pepo* cv. 268NiW, a sample of which has been deposited with NCIMB Ltd under accession number NCIMB 41727 in a PCR reaction with the identical primer pair(s).

In a first step, DNA or cDNA samples are obtained from suitable plant material such as leaf tissue by extracting DNA or RNA using known techniques. Primers that flank a region containing SNPs within the genomic region which is capable of directing or controlling resistance to potyvirus disclosed herein before or within a region linked thereto, are then used to amplify the DNA sample using the polymerase chain reaction (PCR) method.

In the alternative, the presence or absence of the desired allele may be determined by real-time PCR using double-stranded DNA dyes or the fluorescent reporter probe method.

Marker analysis can be done early in plant development using DNA samples extracted from leaf tissue of very young plants or from seed. This allows the identification of plants with a desirable genetic make-up early in the breeding cycle and to discard plants that do not contain the desired, invention-relevant alleles prior to pollination thus reducing the size of the breeding population and reducing the requirements of phenotyping.

Further, by using molecular markers, a distinction can be made between homozygous plants that carry two copies of the desired, invention-relevant allele at the at least one genetic determinant which is capable of directing or controlling resistance to potyvirus and heterozygous plants that carry only one copy and plants that do not contain any copy of the favourable allele(s).

Thus, alternative markers can therefore be developed and used to identify and select plants with an allele or a set of alleles of a qualitative trait locus or loci according to the present invention and as disclosed herein. For example, the nucleotide sequence of the amplification product obtained in PCR amplification using a pair of PCR oligonucleotide primers consisting of
  i. Forward primer of SEQ ID NO: 1 and reverse primer of SEQ ID NO: 2 followed by detection with SEQ ID NO:7 and/or SEQ ID NO:8, and/or;
  ii. Forward primer of SEQ ID NO: 3 and reverse primer of SEQ ID NO: 4 followed by detection with SEQ ID NO:9 and/or SEQ ID NO:10, and/or;
  iii. Forward primer of SEQ ID NO: 5 and reverse primer of SEQ ID NO: 6 followed by detection with SEQ ID NO:11 and/or SEQ ID NO:12; and/or;
  iv. Forward primer of SEQ ID NO: 13 and reverse primer of SEQ ID NO: 14 followed by detection with SEQ ID NO:15 and/or SEQ ID NO:16
can be obtained and new primers or primer pairs designed based on the newly determined nucleotide sequence of the PCR amplification product. Furthermore, the markers according to the invention and disclosed herein before could be positioned on a genetic map of squash or other species and known markers mapping in the same or homolog or ortholog region(s) could be used as starting point for developing new markers.

Accordingly, the markers specifically disclosed in the present invention may also be used in the identification and/or development of new or additional markers associated with resistance to potyvirus, which in turn can then be used in marker assisted breeding and/or the search of recombinants flanking the potyvirus resistant locus, and/or fine-mapping, and/or cloning of the potyvirus resistant loci.

There are several methods or approaches available which can be used to identify and/or develop markers in linkage disequilibrium and/or linked to and/or located in the region of interest, as well as markers that represent the actual causal mutations underlying the potyvirus resistant trait. Without being fully exhaustive, some approaches include:
  use of disclosed sequences/markers in hybridization approaches to identify other sequence in the region of interest.
  use of disclosed sequences/markers in PCR approaches to identify other sequence in the region of interest.
  use of disclosed sequences/markers in PCR approaches to identify other sequence in the region of interest.
  use of disclosed sequences/markers in mapping and/or comparative mapping approaches to identify markers in the same region(s) (positioning of the said at least one genetic determinant which is capable of directing or controlling resistance to potyvirus on other maps).
  use of disclosed sequences/markers in 'in-silico" approaches to identify additional sequences/markers/ (candidate) genes.
  use of disclosed sequences/markers in physical mapping approaches (positioning of the said genetic determinant on a physical map or genome sequence).
  use of disclosed sequences/markers to position the said at least one genetic determinant on other (physical) maps or genomes.
  use of disclosed sequences/markers to select the appropriate individuals allowing the identification of markers in region of interest by genetic approaches.
  use of disclosed information to search for (positional) candidate genes.

For genotyping, mapping or association mapping, DNA is extracted from suitable plant material such as, for example, leaf tissue. In particular, bulks of leaves of a plurality of plants are collected. DNA samples are genotyped using a plurality of polymorphic SSR's, SNPs or any other suitable marker-type covering the entire squash genome.

Joint-analysis of genotypic and phenotypic data can be performed using standard software. Plant introductions and germplasm can be screened for the alleles at the corresponding at least one genetic determinant capable of directing or controlling resistance to potyvirus disclosed herein, based on the nucleotide sequence(s) of the marker(s) at the marker locus/loci linked to said at least one genetic determinant or any other marker known to be located on the same chromosome, and the molecular weight of the allele(s) using one or more of the techniques disclosed herein or known to those skilled in the art.

The nucleic acid sequence of markers, linked markers or the at least one genetic determinant capable of directing or controlling resistance to potyvirus disclosed herein may be determined by methods known to the skilled person. For example, a nucleic acid sequence comprising said at least one genetic determinant or a resistance-conferring part thereof may be isolated from a potyvirus resistant donor plant by fragmenting the genome of said plant and selecting those fragments harbouring one or more markers indicative of said at least one genetic determinant. Subsequently, or alternatively, the marker sequences (or parts thereof) indicative of said resistance locus may be used as (PCR) amplification primers, in order to amplify (a) nucleic acid sequence(s) comprising said resistance locus from a genomic nucleic acid sample or a genome fragment obtained from said plant. The nucleotide sequence of the said at least one genetic determinant, and/or of any additional marker comprised therein, may be obtained by standard sequencing methods.

The present invention therefore also relates to an isolated nucleic acid (preferably DNA but not limited to DNA) sequence that comprises at least one genetic determinant capbale of directing or controlling resistance to potyvirus of the present invention, or a resistance-conferring part thereof. Thus the markers disclosed may be used for the identification and isolation of one or more markers or genes from squash or other vegetable crops that are linked to or encode potyvirus resistance.

The nucleotide sequence of additional markers linked to the said at least one genetic determinant capable of directing or controlling resistance to potyvirus of the present invention may for instance also be resolved by determining the nucleotide sequence of one or more markers associated with the said at least one genetic determinant and designing primers for said sequences of said markers that may then be used to further determine the sequence outside of said markers. For example, the nucleotide sequence of the SNP markers disclosed herein or any other markers predicted in the region of the said at least one genetic determinant and/or linked to said region may be obtained by sequencing the PCR amplification product of said markers by methods well known in the art, or alternatively using the marker sequences in a PCR or as hybridization probes to identify linked nucleotide sequences by for example, but not limited to, BAC screening.

SEED DEPOSIT DETAILS

The following seed samples were deposited with NCIMB, Ferguson Building, Craibstone Estate, Bucksburn, Aberdeen AB21 9YA, Scotland, UK, on Jun. 14, 2010 under the provisions of the Budapest Treaty in the name of Syngenta Participations AG:
NCIMB 41726 *Cucurbita pepo* cv. PP415
NCIMB 41727 *Cucurbita pepo* cv. 268NiW

EMBODIMENTS OF THE INVENTION

1. A cultivated *Cucurbita* plant, preferably *Cucurbita pepo*, comprising at least one genetic determinant which is capable of directing or controlling resistance to potyvirus, preferably 1 or more of MWMV, PRSV, WMV and ZYMV.

2. The plant according to embodiment 1, wherein said genetic determinant is obtainable from the genome of *Cucurbita moschata*, preferably *C. moschata* var. Nigeria.

3. The plant according to embodiment 1 or 2, wherein the said genetic determinant is present in a homozygous state 4. The plant according to embodiment 1 to 3, comprising at least one of said genetic determinant which is capable of directing or controlling resistance to potyvirus infection.

5. The plant according to embodiment 1 to 3, comprising at least two of said genetic determinants which are capable of directing or controlling resistance to potyvirus infection.

6. The plant according to embodiment 1 to 3, comprising at least four of said genetic determinants which are capable of directing or controlling resistance to potyvirus infection, preferably ZYMV and MWMV infection.

7. The plant according to any previous embodiment, wherein
a) the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus ZN, which co-segregates with the potyvirus resistance trait, preferably a ZYMV and PRSV resistance trait, and can be identified in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8; and/or
b) the genetic determinant is complementary to two of the corresponding genetic determinants present in *C. pepo* cv. 268NiW, representative seed of which is deposited at NCIMB under accession number NCIMB 41727, said corresponding genetic determinants being genetically linked to marker locus W1 and/or W2, which co-segregate with the potyvirus resistance trait, preferably a MWMV resistance trait and can be identified in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10
and/or forward primer of SEQ ID NO: 5 and reverse primer of SEQ ID NO: 6 followed by detection with SEQ ID NO:11 and/or SEQ ID NO:12; and/or
c) the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus Ni+, which co-segregates with the potyvirus resistance trait, preferably a ZYMV resistance trait, more preferably a ZYMV strain Nivir resistance trait, and can be identified in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16

8. The plant according to any previous embodiment, wherein
a) the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus ZN which co-segregates with the potyvirus resistance trait, preferably a ZYMV and PRSV resistance trait, and can be identified in the *C. pepo* cv. 268NiW genome in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8; and/or b) the genetic determinant is complementary to two of the corresponding genetic determinants present in *C. pepo* cv. 268NiW, representative seed of which is deposited at NCIMB under accession number NCIMB 41727, said corresponding genetic determinants being genetically linked to marker locus W1 and/or W2 which co-segregate with the potyvirus resistance trait, preferably a MWMV resistance trait and can be identified in the *C. pepo* cv. 268NiW genome in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10;

and/or forward primer of SEQ ID NO: 5 and reverse primer of SEQ ID NO: 6 followed by detection with SEQ ID NO:11 and/or SEQ ID NO:12; and/or c) the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus Ni+ which co-segregates with the potyvirus resistance trait, preferably a ZYMV resistance trait, more preferably a ZYMV strain Nivir resistance trait, and can be identified in the *C. pepo* cv. 268NiW genome in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16

9. The plant according to any previous embodiment, wherein a) the genetic determinant is genetically linked to marker locus ZN, which co-segregates with the potyvirus resistance trait, preferably a ZYMV and PRSV resistance trait, and can be identified in the genome of said plant in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8; and/or b) the genetic determinant is genetically linked to marker locus W2, which co-segregates with the potyvirus resistance trait, preferably a MWMV resistance trait and can be identified in the genome of said plant in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10;

and/or forward primer of SEQ ID NO: 5 and reverse primer of SEQ ID NO: 6 followed by detection with SEQ ID NO:11 and/or SEQ ID NO:12; and/or c) the genetic determinant is genetically linked to marker locus Ni+, which co-segregates with the potyvirus resistance trait, preferably a ZYMV resistance trait, more preferably a ZYMV strain Nivir resistance trait, and can be identified in the genome of said plant in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16.

10. The plant according to any previous embodiment, wherein the genetic determinant(s) is/are recessive.

11. The plant according to any previous embodiment, wherein the plant is a non-transgenic squash plant.

12. The plant according to any previous embodiment, wherein the plant is an inbred, a dihaploid or a hybrid.

13. The plant according to any previous embodiment, wherein the plant is male sterile.

14. Plant material obtainable from a plant according to any of the preceding embodiments including, but without being limited thereto, leaves, stems, roots, flowers or flower parts, fruits, pollen, egg cells, zygotes, seeds, cuttings, cell or tissue cultures, or any other part or product of the plant which still exhibits a potyvirus resistant phenotype, particularly when grown into a plant.

15. Plant parts of a plant according to any of the preceding embodiments including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits a potyvirus resistant phenotype, particularly when grown into a plant.

16. Seed of a squash plant according to any previous embodiment which is capable of growing a potyvirus resistant squash plant.

17. Seed according to embodiment 16, wherein said seeds are hybrid seeds.

18. Seed according to embodiment 17, deposited at NCIMB Ltd under accession number 41727.

19. Use of a seed of embodiments 16 to 18 for growing a potyvirus resistant squash plant.

20. A kit for the detection of a genetic determinant which is capable of directing or controlling resistance to potyvirus in a squash plant, wherein said kit comprises one PCR oligonucleotide primer or a pair of PCR oligonucleotide primers, which is able to amplify a DNA marker linked to the genetic determinant, and wherein said DNA maker can be amplified in a PCR with a pair of PCR oligonucleotide primers selected from a) forward primer of SEQ ID NO: 1 and a reverse primer of SEQ ID NO: 2 followed by detection with SEQ ID NO:7 and/or SEQ ID NO:8 and/or;

b) forward primer of SEQ ID NO: 3 and a reverse primer of SEQ ID NO: 4 followed by detection with SEQ ID NO:9 and/or SEQ ID NO:10 and/or:

c) forward primer of SEQ ID NO: 5 and a reverse primer of SEQ ID NO: 6 followed by detection with SEQ ID NO:11 and/or SEQ ID NO:12; and/or d) forward primer of SEQ ID NO: 13 and a reverse primer of SEQ ID NO: 14 followed by detection with SEQ ID NO:15 and/or SEQ ID NO:16.

21. A DNA marker that is linked to the genetic determinant which is capable of directing or controlling resistance to potyvirus and can be amplified in a PCR with a pair of PCR oligonucleotide primers selected from a) forward primer of SEQ ID NO: 1 and a reverse primer of SEQ ID NO: 2 followed by detection with SEQ ID NO:7 and/or SEQ ID NO:8 and/or;

b) forward primer of SEQ ID NO: 3 and a reverse primer of SEQ ID NO: 4 followed by detection with SEQ ID NO:9 and/or SEQ ID NO:10 and/or;

c) forward primer of SEQ ID NO: 5 and a reverse primer of SEQ ID NO: 6 followed by detection with SEQ ID NO:11 and/or SEQ ID NO:12; and/or d) forward primer of SEQ ID NO: 13 and a reverse primer of SEQ ID NO: 14 followed by detection with SEQ ID NO:15 and/or SEQ ID NO:16

22. Use of any one of the DNA markers according to embodiment 21 for diagnostic selection of a genetic determinant which is capable of directing or controlling resistance to potyvirus in squash.

23. Use of any one of the DNA markers according to embodiments 21-22 for identifying in a plant the presence of a genetic determinant which is capable of directing or controlling resistance to potyvirus and/or for monitoring the introgression of the genetic determinant which is capable of directing or controlling resistance to potyvirus in squash.

24. Polynucleotide obtainable in a PCR by amplification of a DNA fragment with a pair of PCR oligonucleotide primers selected from a) forward primer of SEQ ID NO: 1 and a reverse primer of SEQ ID NO: 2 followed by detection with SEQ ID NO:7 and/or SEQ ID NO:8 and/or;

b) forward primer of SEQ ID NO: 3 and a reverse primer of SEQ ID NO: 4 followed by detection with SEQ ID NO:9 and/or SEQ ID NO:10 and/or;

c) forward primer of SEQ ID NO: 5 and a reverse primer of SEQ ID NO: 6 followed by detection with SEQ ID NO:11 and/or SEQ ID NO:12; and/or;

d) forward primer of SEQ ID NO: 13 and a reverse primer of SEQ ID NO: 14 followed by detection with SEQ ID NO:15 and/or SEQ ID NO:16;

said polynucleotide containing a DNA marker that is statistically correlated and thus genetically linked to a genetic determinant which is capable of directing or controlling resistance to potyvirus, and wherein said polynucleotide corresponds to an amplification product obtainable from *C. pepo* cv. 268NiW, representative seed of which is deposited at NCIMB under accession number NCIMB 41727, in a PCR with the same primer pairs provided that the respective marker locus is still present in said *C. pepo* cv. 268NiW plant and/or can be considered an allele thereof.

25. A polynucleotide that has at least 90%, particularly at least 95%, particularly at least 96%, particularly at least 97%, particularly at least 98%, particularly at least 99% sequence identity with the sequence of a polynucleotide of embodiment 24.

26. A polynucleotide exhibiting a nucleotide sequence that hybridizes to the nucleotide sequence of the polynucleotide of embodiment 25.

27. A method for introducing at least one genetic determinant which is capable of directing or controlling resistance to potyvirus into a squash plant lacking said genetic determinant comprising:

a) obtaining a first squash plant according to any one of the preceding embodiments;

b) crossing said first squash plant with a second squash plant, wherein said second squash plant lacks said allele; and c) identifying a plant resulting from the cross exhibiting increased resistance to potyvirus and comprising at least one DNA marker co-segregating with said potyvirus resistance; and d) optionally, isolating said plant and e) optionally, back-crossing said plant with the first or second squash plant.

28. A method for obtaining seed of a plant according to any of the preceding embodiments comprising the steps of:

a) obtaining a first squash plant according to any one of the preceding embodiments;

b) crossing said first squash plant with a second squash plant, wherein said second squash plant lacks said genetic determinant; and c) identifying a plant resulting from the cross exhibiting increased resistance to potyvirus and comprising at least one DNA marker co-segregating with said potyvirus resistance; and d) harvesting progeny seed from said cross comprising at least one DNA marker co-segregating with said potyvirus resistance.

29. A method according to any one of embodiments 27 or 28, wherein in step c) a plant resulting from the cross and comprising a at least one genetic determinant capable of directing or controlling resistance to potyvirus can be identified in a PCR by amplification of a DNA fragment with a pair of PCR oligonucleotide primers selected from a) forward primer of SEQ ID NO: 1 and a reverse primer of SEQ ID NO: 2 followed by detection with SEQ ID NO:7 and/or SEQ ID NO:8 and/or;

b) forward primer of SEQ ID NO: 3 and a reverse primer of SEQ ID NO: 4 followed by detection with SEQ ID NO:9 and/or SEQ ID NO:10 and/or;

c) forward primer of SEQ ID NO: 5 and a reverse primer of SEQ ID NO: 6 followed by detection with SEQ ID NO:11 and/or SEQ ID NO:12; and/or d) forward primer of SEQ ID NO: 13 and a reverse primer of SEQ ID NO: 14 followed by detection with SEQ ID NO:15 and/or SEQ ID NO:16.

30. A method according to embodiment 29, wherein the fragment size of the amplification product of one or more primer pairs is determined.

31. A method for producing a squash plant exhibiting resistance to potyvirus, preferably to 1 or more of MWMV, PRSV, WMV and ZYMV comprising the steps of:

a) Selecting a squash plant comprising at least one genetic determinant which is capable of directing or controlling resistance to potyvirus, wherein said genetic determinant is obtainable from the genome of *C. pepo* cv. 268NiW and is genetically linked to at least one marker locus, which co-segregates with resistance to potyvirus, and can be identified in a PCR by at least one pair of PCR oligonucleotide primers comprising i. Forward primer of SEQ ID NO: 1 and reverse primer of SEQ ID NO: 2 followed by detection with SEQ ID NO:7 and/or SEQ ID NO:8, and/or;

ii. Forward primer of SEQ ID NO: 3 and reverse primer of SEQ ID NO: 4 followed by detection with SEQ ID NO:9 and/or SEQ ID NO:10, and/or;

iii. Forward primer of SEQ ID NO: 5 and reverse primer of SEQ ID NO: 6 followed by detection with SEQ ID NO:11 and/or SEQ ID NO:12, and/or;

iv. Forward primer of SEQ ID NO: 13 and a reverse primer of SEQ ID NO: 14 followed by detection with SEQ ID NO:15 and/or SEQ ID NO:16, and/or;

v. A forward and reverse primer capable of identifying a marker locus which co-segregates with at least one of said potyvirus resistant phenotypes;

b) Crossing said plant of step a) with a squash plant which is susceptible to potyvirus, or exhibits an intermediate level of resistance to at least one of said potyviruses; and c) Selecting a progeny from said cross which exhibits a resistance phenotype to potyvirus, and wherein said resistance phenotype(s) segregates with said at least one marker locus of step a).

32. The method for producing a squash plant exhibiting resistance to potyvirus, preferably at least one of ZYMV and MWMV according to embodiment 31, comprising the steps of:

a) Selecting a squash plant comprising at least one genetic determinant which is capable of directing or controlling resistance to potyvirus, wherein said genetic determinant is obtainable from the genome of *C. pepo* cv. 268NiW and is genetically linked to at least one marker locus, which co-segregates with resistance to potyvirus, and can be identified in a PCR by at least one pair of PCR oligonucleotide primers comprising
  i. Forward primer of SEQ ID NO: 1 and reverse primer of SEQ ID NO: 2 followed by detection with SEQ ID NO:7 and/or SEQ ID NO:8 if the marker locus is ZN and/or;
  ii. Forward primer of SEQ ID NO: 3 and reverse primer of SEQ ID NO: 4 followed by detection with SEQ ID NO:9 and/or SEQ ID NO:10 if the marker locus is W1 and/or;
  iii. Forward primer of SEQ ID NO: 5 and reverse primer of SEQ ID NO: 6 followed by detection with SEQ ID NO:11 and/or SEQ ID NO:12 if the marker locus is W2;
  iv. Forward primer of SEQ ID NO: 13 and reverse primer of SEQ ID NO: 14 followed by detection with SEQ ID NO:15 and/or SEQ ID NO:16 if the marker locus is Ni+;
  b) Crossing said plant of step a) with a squash plant which is susceptible to potyvirus, or exhibits an intermediate level of resistance to at least one of said potyviruses; and
  c) Selecting a progeny from said cross which exhibits a resistance phenotype to potyvirus, and wherein said resistance phenotype(s) segregates with said at least one marker locus of step a).

33. The method according to embodiment 31 or 32, wherein the plant selected in step a) comprises at least two genetic determinants which are capable of directing or controlling resistance to potyvirus; and the selected progeny in step c) exhibits a potyvirus resistance phenotype, and wherein said resistance phenotypes segregate with two marker loci of step a).

34. The method according to embodiment 31 or 32, wherein the plant selected in step a) comprises at least three genetic determinants which are capable of directing or controlling resistance to potyvirus, preferably to ZYMV and MWMV; and the selected progeny in step c) exhibits a resistance phenotype to potyvirus, preferably to ZYMV and MWMV and wherein said resistance phenotypes segregate with the marker loci of step a).

35. The method according to any previous embodiments 31 to 34 wherein the donor plant of step a) is a plant of any previous embodiment 1 to 13.

36. The method according to embodiments 31 to 35 comprising the additional step of backcrossing the virus resistant plant obtained in step c) with the susceptible squash plant, or intermediate resistant squash plant, of step b).

37. A method for producing hybrid seeds of squash resistant to potyvirus comprising
  a) planting a male-sterile female plant and a male-fertile plant, wherein one of said male-sterile female plant or male fertile plant is a plant according to any of previous embodiments 1 to 13,
  b) effecting cross pollination between both lines,
  c) growing the plant till fruit setting,
  d) collecting the fruits and
  e) obtaining the hybrid seeds.

38. A method for obtaining a potyvirus resistant squash plant comprising
  a) Obtaining a plant of any previous embodiment or by a method of any previous embodiment;
  b) Crossing said plant with a potyvirus susceptible plant or an intermediate resistant squash plant;
  c) Rescuing an embryo resulting from the cross of step b);
  d) Regenerating a plant from said embryo of step c); and
  e) Selecting a plant of step d) that is resistant potyvirus, preferably to at least one of ZYMV and MWMV.

39. A method for obtaining squash fruit resistant to potyvirus comprising
  a) Sowing seed of a plant according to any one of any previous embodiment or obtained by a method according to any one of any previous embodiment; and
  b) Growing said plant in order to produce fruit and harvesting the fruit produced by said plant.

40. A genetic determinant which is capable of directing or controlling resistance to potyvirus wherein said genetic determinant is obtainable from the genome of *C. pepo* cv. 268NiW, wherein
  a) the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus ZN, which co-segregates with the potyvirus resistance trait, preferably a ZYMV and PRSV resistance trait, and can be identified in a PCR by amplification of a DNA fragment with the pair of oligonucleotide primers: forward primer of SEQ ID NO: 1 and reverse primer of SEQ ID NO: 2 followed by detection with SEQ ID NO:7 and/or SEQ ID NO:8; and/or
  b) the genetic determinant is complementary to at least one of the corresponding genetic determinants present in *C. pepo* cv. 268NiW, representative seed of which is deposited at NCIMB under accession number NCIMB 41727, said corresponding genetic determinants being genetically linked to marker loci W1 and/or W2, which co-segregates with the potyvirus resistance trait, preferably a MWMV resistance trait and can be identified in a PCR by amplification of a DNA fragment with the pair of oligonucleotide primers: forward primer of SEQ ID NO: 3 and reverse primer of SEQ ID NO: 4 followed by detection with SEQ ID NO:9 and/or SEQ ID NO:10;
  and/or forward primer of SEQ ID NO: 5 and reverse primer of SEQ ID NO: 6 followed by detection with SEQ ID NO:11 and/or SEQ ID NO:12; and/or
  c) the genetic determinant is complementary to the corresponding genetic determinant present in *C. pepo* cv. 268NiW, representative seed of which is deposited at NCIMB under accession number NCIMB 41727, said corresponding genetic determinant being genetically linked to marker locus Ni+, which co-segregates with the potyvirus resistance trait, preferably a ZYMV resistance trait, more preferably a ZYMV strain Nivir resistance trait, and can be identified in a PCR by amplification of a DNA fragment with the pair of oligonucleotide primers: forward primer of SEQ ID NO: 13 and reverse primer of SEQ ID NO: 14 followed by detection with SEQ ID NO:15 and/or SEQ ID NO:16.

41. A method of identifying a squash plant comprising at least one genetic determinant which is capable of directing or controlling resistance to potyvirus, preferably to at least one of ZYMV and MWMV wherein said genetic determinant is obtainable from the genome of *C. pepo* cv. 268NiW and is genetically linked to at least one marker locus, which co-segregates with at least one of said potyvirus resistant phenotypes and can be identified in a PCR by at least one pair of PCR oligonucleotide primers comprising
  i. Forward primer of SEQ ID NO: 1 and reverse primer of SEQ ID NO: 2 followed by detection with SEQ ID NO:7 and/or SEQ ID NO:8 if the marker locus is ZN, or;

ii. Forward primer of SEQ ID NO: 3 and reverse primer of SEQ ID NO: 4 followed by detection with SEQ ID NO:9 and/or SEQ ID NO:10 if the marker locus is W1, or;
iii. Forward primer of SEQ ID NO: 5 and reverse primer of SEQ ID NO: 6 followed by detection with SEQ ID NO:11 and/or SEQ ID NO:12 if the marker locus is W2, or;
iv. Forward primer of SEQ ID NO: 13 and reverse primer of SEQ ID NO: 14 followed by detection with SEQ ID NO:15 and/or SEQ ID NO:16 if the marker locus is Ni"

42. Use of potyvirus resistant propagating material from a squash plant according to any one of the preceding embodiments for growing a potyvirus resistant squash plant in order to produce fruit and harvest said fruit.

EXAMPLES

Example 1

Discovery of Markers Closely Linked to ZYMV and MWMV Resistance Genes in Squash 1. 1 Materials For marker discovery purposes, F2 populations segregating for ZYMV—(R line [PP452]×S line [TOSCA]) and MWMV (S line [PP477]×R line [PP477/(PP415/(PP419/(Nigeria/PP432)]) resistance genes from *Cucurbita moschata* cv Nigeria were generated and sampled; and their corresponding F3 progenies phenotyped for ZYMV and MWMV resistance, respectively. Predictive value of developed assays was assessed by genotyping a diverse verification panel consisting of 96 squash lines and varieties corresponding to different types and market segments.

1. 2 Marker Discovery

Bulked Segregant Analysis (BSA) using Random Amplified Polymorphism DNA (RAPD) markers (from Operon technologies, Alameda, Calif.; and University of British Columbia, Vancouver, Canada); was performed on different F2 DNA pools with opposed resistant and susceptible phenotypes. Identified candidate markers from BSA screening (RAPD bands showing clear presence/absence patterns between the F2 R and S bulks) were further tested for linkage in the individual members of the F2 population; and the most closely linked markers, selected for further specific assay development.

For ZYMV, a single RAPD marker, OPBB09_451; showing a perfect correlation (co-segregation) with the ZYMV resistance phenotype in the F2 population, was selected for Taqman End Point Reading (EPR) assay development.

For MWMV, RAPD markers correlated with the MWMV resistance phenotype were mapped in two different loci (QTLs) and best markers, OPAR13_507 and UBC385_656, showing the highest association (linkage) with QTL1 and QTL2 respectively, were selected.

For Ni+, a BSA was performed by re-sequencing the two bulks. Obtained reads have been aligned to a reference sequence of Squash and SNPs have been detected. The most closely linked SNPs were then selected for further specific Taqman EPR assay development.

1.3 Taqman EPR Assay Development

All plant DNA was isolated according to the Potassium acetate+Proteinase K protocol. For allelic sequencing up to 3 different PCR primer combinations were designed at 5' and 3' ends of selected RAPD candidate fragments. PCR products and DNA sequences of these markers were obtained using lines from a panel of resistant and susceptible lines.

Taqman EPR assay development was based upon discovered allele specific SNPs of the sequence panel. The EPR assay development was performed according to standard guidelines including testing of different PCR mixes, DNA concentrations and annealing temperatures. Probes are FAM- and VIC MGB Taqman probes (Eurogentec).

1.4 Taqman EPR Assay Protocol

1. Isolate DNA genomic with standard DNA extraction Potassium acetate+Proteinase K protocol. Finally, 150 µl of DNA solution was obtained.
2. Dilute template DNA to 1/15.
3. Pipette 4 µl of each diluted DNA sample into individual 384 PCR plate wells.
4. Cover and centrifuge the plate and place on ice.
5. Make the master mix. Following is per reaction:

| Vegetable project mix Platinum | Volume (µl) | Final Concentration |
| --- | --- | --- |
| Platinum buffer 10x | 1 | 1x |
| MgCl2 50 mM | 0.6 | 3 mM |
| dNTP 10 mM (2.5 mM each) | 0.8 | 0.8 mM (0.2 mM each) |
| Taq platinum 5 U/µl | 0.066 | 0.33U |
| ZN R allele VIC-MGB-NFQ probe 10 µM | 0.1 | 100 nM |
| ZN S allele FAM-MGB-NFQ probe 10 µM | 0.1 | 100 nM |
| ZN sense primer 12.5 µM | 0.16 | 200 nM |
| ZN anti-sense primer 12.5 µM | 0.16 | 200 nM |
| ROX 50x | 0.1 | 0.5x |
| Qsp H2O | 2.914 | |
| Total volume | 6 | |

6. Add 6 µl master mix into each PCR plate well (with the 4 µl template DNA already in)
7. Spin down briefly.
8. Load the 384 plate on PCR machine
9. PCR program on ABI GENEAMP PCR 9700-384 plate format as follows:
   2 min 94° C.
   15 sec 94° C.
   1 min 60° C.
   40×
   5 min 72° C.
10. Read the plate at AB17900.

1.5 EPR Assay Primer and Probe Sequences
1.5.1. ZYMV-Nigeria

```
Forward primer:
5' AGGTTTCATGGGCTTTTAATGG 3'      (SEQ ID NO: 1)

Reverse primer:
5' CGTGAGCCTAAAACGGTTAATG 3'      (SEQ ID NO: 2)

Resistant allele specific probe:
FAM-CACTTCCCAGCCCAAAT-MGB-NFQ    (SEQ ID NO: 7)

Susceptible allele specific probe:
VIC-CACTTTCCAGCCCAAAT-MGB-NFQ    (SEQ ID NO: 8)

Ni+
Forward primer:
5' TTGCATGTTCCTTGGATGGGT 3'      (SEQ ID NO: 13)

Reverse primer:
5' GGCAACCTCTGTCCAATTTCTTTC 3'   (SEQ ID NO: 14)

Resistant allele specific probe:
FAM-AGTTGCGACTTTCCA-MGB-NFQ      (SEQ ID NO: 15)

Susceptible allele specific probe:
TET-AGTTGCGACTTTTCATT-MGB-NFQ    (SEQ ID NO: 16)
```

1.5.2. MWMV-Nigeria

```
1.5.2.1 QTL1
Forward primer:
                                    (SEQ ID NO: 3)
5' GGGCAAAGAAGATCTTGTCTAGAAAG 3'

Reverse primer:
                                    (SEQ ID NO: 4)
5' GTTTTTGTGCAGTGTGCATCTGT 3'

Resistant allele specific probe:
                                    (SEQ ID NO: 9)
FAM-TCATTGCACCCAACATG-MGB-NFQ Susceptible allele specific probe:
                                    (SEQ ID NO: 10)
VIC-TCATTGCACTCAACATGG-MGB-NFQ 1.5.2.1 QTL2
Forward primer:
                                    (SEQ ID NO: 5)
5' TTGTGTTTATATGTATGTGTGCGAG 3'

Reverse primer:
                                    (SEQ ID NO: 6)
5' TTTCTAGATCTCAGTGTAAGAGAACACA 3'

Resistant allele specific probe:
                                    (SEQ ID NO: 11)
FAM-TTTGTTTGCTTGAGCTGG-MGB-NFQ Susceptible allele specific probe:
                                    (SEQ ID NO: 12)
VIC-TTTGTTCGATTGAGCTGG-MGB-NFQ
```

Example 2

Disease Test Protocol

2.1 Use of Protocol

The following protocol is applicable for all virus (CMV, ZYMV, WMV, MWMV) on squash as well as *Cucurbita* sp. and cucumber (*Cucumis sativus* sp.).

2.2 Conservation of the Strain

Freshly infected leaves (1 g) were weighed. The leaves were then cut finely with a scalpel and put on a paper weighing tray. The weighing tray was put on a Petri dish (55 mm) that contains anhydride chlorure calcium. The box was sealed with parafilm. The name of the strain, the date of the conservation and the weight of fresh leaves prepared were indicated on the box and the number of boxes were recorded. The dishes were kept in the drawer "vegetables" in the fridge.

2.3 Multiplication of Virus from Dehydrated Preparation

One or more terrines of a susceptible variety were sown. Inoculation was made from dehydrated preparation (see below inoculation of the tests) when the plants are at the "coytyledons" stage. After 1 week to 10 days, the first symptoms would appear and is the stage at which the virus is most aggressive.

2.4 Preparation of the Inoculum

Young infected leaves were picked from the terrine. For 1 gram of leaves, 0.1 gram of coal and 4 cc of buffer solution were prepared. The leaves were crushed before adding the coal and finally the buffer solution. The carborundum was sprinkled into the mix. With 1 gram of fresh leaves, 2-3 terrines could be inoculated (1 terrine=80-100 plants).

2.5 Inoculation of the Tests

The inoculums were put on a bed of ice. The plants were inoculated at the cotyledon stage. The cotyledons were rubbed with the inoculums, renewing the solution each hour if necessary. After drying for 15 mins, the plant was then watered. The first reading could be taken 5 to 6 days after inoculation. A second reading could then be taken after 7 to 10 days to confirm and complete the information. To end the test, the leaves were sealed in a plastic bag and put in the biological waste. The best temperature conditions for carrying out the test are 25° C.±2° during the day and 20° C.±2° during the night.

2.6 Chronology

Day 0-8 SOWING OF TERRINES OF MULTIPLICATION
Day 0-2 INOCULATION OF THE TERRINES
Day 0 SOWING OF THE TESTS
Day 0+6 INOCULATION OF THE TESTS
Day 0+14 BEGINNING OF THE READING
Day 0+30 DESTRUCTION OF THE TESTS

Example 3

Guidelines for Potyvirus Pathology Tests on Summer Squash (*Cucurbita pepo*)

3.1 Rating Guidelines

The following guidelines were used to determine the extent of ZYMV, WMV, PRSV, MWMV infection on leaves and fruits. Readings, evaluation and ratings were made all along the crop, from $3^{rd}$ leaf stage until adult plant stage (with botanical mature fruits).

Ratings are done on a scale from 1 to 9 according to the following guidelines, examples of which are shown in FIGS. 1 to 9.

TABLE 1

Guidelines for potyvirus tests

| Rating | Symptoms on leaves | Symptoms on fruits |
|---|---|---|
| 1 | Severe deformation, filiformism. Stunting of leaves and petioles. Plant stops growing. | Color breaking. Severe bumpings on fruits. Mishaped ovaries. No marketable fruits. |
| 2 | Severe deformation, filiformism. Stunting leaves and petioles. | Color breaking. Severe bumpings on fruits. Mishaped ovaries. No marketable fruits. |
| 3 | Severe mosaic symptoms, sometimes filiformism on leaves. | Many symptoms on each fruit, mainly discoloured ring shaped zones, sometimes bumping. |
| 4 | Severe mosaic symptoms. | Many symptoms on each fruit, mainly discoloured ring shaped zones. |
| 5 | Mosaic symptoms on leaves. | Small depression zones on fruits. |
| 6 | Mosaic symptoms on leaves, not every leaf. | Small depression zones on fruits, some fruits may be free of symptoms. |

TABLE 1-continued

Guidelines for potyvirus tests

| Rating | Symptoms on leaves | Symptoms on fruits |
|---|---|---|
| 7 | Few yellow spotting on leaves. | Few symptoms, generally small discolored depressions on fruits (commercial and pure botanical), but not on every fruit. |
| 8 | No symptoms after 3$^{rd}$ leaf. | Absence of symptoms on commercial fruits and botanical mature fruits. |
| 9 | No symptoms. | Absence of symptoms on commercial fruits and botanical mature fruits. |

TABLE 2

Ratings for deposit line 268Niw on several screens
For ZYMV and WMV, a distinction is made between mild and severe form of the strains.

| Virus/strain | Susceptible check PP547 | Line 268 | Line 268Ni+ | Line 268Niw (NCIMB 41427) |
|---|---|---|---|---|
| ZYMV mild strain | 2 | 7 | 8 | 9 |
| ZYMV severe strain | 1 | 2 | 6 | 8 |
| WMV mild strain | 5 | 6 | 8 | 9 |
| WMV severe strain | 2 | 2 | 6 | 8 |
| MWMV/INRA | 1 | 1 | 5 | 7 |
| PRSV/E2 | 2 | 4 | 6 | 8 |

The invention claimed is:

1. A cultivated *Cucurbita pepo* plant comprising two recessive genetic determinants which are capable of directing or controlling resistance to potyvirus, wherein said genetic determinants are genetic determinants of *Cucurbita pepo* cv. 268NiW, representative seed of which is deposited at NCIMB under accession number NCIMB 41727, and said genetic determinant are:

a) a genetic determinant that is genetically linked to marker locus W1, which marker locus comprises a single nucleotide polymorphism (SNP) and co-segregates with the potyvirus resistance trait and said marker locus can be identified in the genome of said plant in a PCR by amplification of a DNA fragment containing the marker locus with the pair of oligonucleotide primers: forward primer of SEQ ID NO: 3 and reverse primer of SEQ ID NO: 4 followed by detection of the marker locus with resistant allele specific probe SEQ ID NO:9, wherein the marker comprises a nucleotide G corresponding to position 10 of SEQ ID NO: 9; and, b) a genetic determinant that is genetically linked to marker locus W2, which marker locus comprises a single nucleotide polymorphism (SNP) and co-segregates with the potyvirus resistance trait and said marker locus can be identified in the genome of said plant in a PCR by amplification of a DNA fragment containing the marker locus with the pair of oligonucleotide primers: forward primer of SEQ ID NO: 5 and reverse primer of SEQ ID NO: 6 followed by detection of the marker locus with resistant allele specific probe SEQ ID NO:11, wherein the marker comprises a nucleotide A corresponding to position 7 of SEQ ID NO: 11 and a nucleotide G corresponding to position 9 of SEQ ID NO: 11.

2. The plant according to claim 1, wherein the plant is a squash plant.

3. Seed of a squash plant according to claim 2 which is capable of growing a potyvirus resistant squash plant comprising the genetic determinant which is capable of directing or controlling resistance to potyvirus.

4. The plant according to claim 1, wherein the plant is resistant to *Papaya* Ringspot Virus (PRSV).

5. The plant according to claim 1, wherein said plant further comprises:

a genetic determinant that is genetically linked to marker locus ZN, which marker locus comprises a single nucleotide polymorphism (SNP) and co-segregates with the potyvirus resistance trait and said marker locus can be identified in the genome of said plant in a PCR by amplification of a DNA fragment containing the marker locus with the pair of oligonucleotide primers: forward primer of SEQ ID NO: 1 and reverse primer of SEQ ID NO: 2 followed by detection of the marker locus with resistant allele specific probe SEQ ID NO:7, wherein the marker comprises a nucleotide G corresponding to position 6 of SEQ ID NO: 7.

6. The plant according to claim 5, wherein the plant is a squash plant.

7. Seed of a squash plant according to claim 6 which is capable of growing a potyvirus resistant squash plant comprising the genetic determinants which are capable of directing or controlling resistance to potyvirus.

8. The plant according to claim 5, wherein the plant is resistant to ZYMV.

9. The plant according to claim 5, wherein the plant is resistant to MWMV and ZYMV.

* * * * *